United States Patent [19]
Leser

[11] Patent Number: 5,270,535
[45] Date of Patent: Dec. 14, 1993

[54] MOUNTING FRAMEWORK FOR CONTACTLESS TESTING DEVICES FOR MOLDED OBJECTS AT HIGH TEMPERATURE HAVING A NONDEFORMABLE STRUCTURE WITH CONTROLLED DISPLACEMENTS

[75] Inventor: Jacques Leser, Lunel, France

[73] Assignee: Verrerie du Languedoc & CIE, Vergeze, France

[21] Appl. No.: 967,874

[22] Filed: Oct. 28, 1992

[30] Foreign Application Priority Data

Oct. 30, 1991 [FR] France .................. 91 13414

[51] Int. Cl.$^5$ .............................................. G01N 9/04
[52] U.S. Cl. .................. 250/223 B; 356/240; 250/561
[58] Field of Search .......... 250/223 B, 223 R, 561, 250/562; 356/240, 427, 428; 209/587

[56] References Cited
U.S. PATENT DOCUMENTS

| | | |
|---|---|---|
| 3,245,533 | 4/1966 | Rottmann . |
| 3,956,632 | 5/1976 | Hall et al. . |
| 4,239,116 | 12/1980 | Eisenberg et al. .............. 250/223 B |
| 4,476,533 | 10/1984 | Daudt et al. . |
| 4,693,376 | 9/1987 | Marion et al. .................. 250/223 B |

FOREIGN PATENT DOCUMENTS

0177004  4/1986  European Pat. Off. .

Primary Examiner—David C. Nelms
Assistant Examiner—Que T. Le
Attorney, Agent, or Firm—Helfgott & Karas

[57] ABSTRACT

A mounting framework for mounting contactless testing devices for testing molded objects, in particular glass objects, at high temperature, comprises a rigid frame structure positioned above a conveyor belt on which glass bottles at high temperature move. The conveyor belt is driven with respect to a conveyor frame with an adjustable inclination in the same vertical plane. The mounting framework is placed astride above the belt. The framework comprises two units defining two parallel reference planes and constituting a nondeformable structure which is not connected to the frame of the conveyor and is supported on the ground by three jacks with controlled displacements. Three light sources emit light rays whose characteristics depend on the inclination of the conveyor belt. The light sources interact with networks of linear photodiodes capable of generating electrical signals for controlling the jacks in order to maintain the aforementioned reference planes of the framework continuously parallel to the plane of the conveyor belt whatever its inclination. A plurality of contactless testing devices may be mounted on the framework.

10 Claims, 8 Drawing Sheets

MOUNTING FRAMEWORK FOR CONTACTLESS TESTING DEVICES FOR MOLDED OBJECTS AT HIGH TEMPERATURE HAVING A NONDEFORMABLE STRUCTURE WITH CONTROLLED DISPLACEMENTS

BACKGROUND OF THE INVENTION

The present invention relates to a framework making it possible to mount a variety of contactless testing devices, for molded objects, in particular glass objects at a high temperature such as bottles, automatically manufactured at a high rate.

The manufacture of molded objects and in particular glass bottles requires high-precision manufacturing testing in particular relating to leaktightness, the verticality and other shape characteristics and furthermore intended to eliminate manufacturing defects such as internal inclusions in the molded material forming tones, filaments of glass between the two walls of the bottle (which are commonly called "tapezes"), excess material on the collar of the neck, etc.

It is known to perform multiple, partly manual tests on cold objects, that is to say approximately one hour after manufacturing. In order to reduce the time elapsing between manufacturing and testing and thus to be able to act on the manufacturing process in order to decrease the number of defects, a hot testing method and device have already been developed allowing negative feedback on the control system of the manufacturing machine, as described in European Patent 177,004 corresponding to U.S. Pat. No. 4,694,158 (VERRERIE du LANGUEDOC). Such a method for automatic contactless testing of bottles at high temperature, immediately on output from the molding machine, has a large number of advantages.

For implementing testing encompassing a large number of defects it is however necessary to provide a plurality of optical or optoelectronic testing devices along the path of transport of the molded objects such as glass bottles.

The molding machines normally used include a continuously driven conveyor belt on which the molded objects, such as glass bottles, are arranged by the action of a gripper which takes the bottle out of the mold, the bottle then being pushed onto the conveyor by means of a pivoting push rod. The level of the gripper for gripping the molded bottle is constant with respect to the ground on which the molding machine is installed. Now, the machine is generally capable of manufacturing bottles of variable sizes so that it is necessary when changing the manufacturing to modify the level of the conveyor belt with respect to the ground at the location of the molding machine. At the output of the molding machine, the bottles transported on the conveyor are subjected to various treatments, before being conveyed into an oven called a "lehr" inside which the glass bottles are subjected to a final annealing heat treatment. Taking into account the dimensions of the lehr, the input level of the latter is also constant with respect to the ground. It will be understood that under these conditions, it is necessary to provide the possibility of adjusting the inclination of the conveyor belt in a vertical plane between the molding machine and the lehr. These inclination modifications of the conveyor belt lead to additional difficulties for the mounting and arrangement of the various testing instruments necessary for implementing an automatic testing method for molded objects along their passage on the conveyor belt between the molding machine and the lehr. It is furthermore expedient, independently of such an inclination adjustment in a vertical plane, to adjust for possible inclination defects of the conveyor belt with respect to a horizontal plane. The mounting of these test instruments directly on the frame of the conveyor belt may not be envisaged because of the strong vibrations to which the frame is subjected.

SUMMARY OF THE INVENTION

An object of the present invention is to solve the above problems and to allow a reliable and precise installation of a set of testing devices for implementing an automatic contactless testing method for molded objects, in particular glass bottles, at high temperature.

The mounting framework for contactless testing devices according to the invention making it possible to test molded objects, in particular glass objects, at high temperature and, in particular bottles, placed on a conveyor belt driven with respect to a frame with adjustable inclination in a vertical plane, comprises means defining two parallel reference planes and being connected together by rigid columns so as to define a nondeformable structure straddling the conveyor belt in the manner of a bridge. The nondeformable structure is not connected to the frame of the conveyor but is supported by means of three jacks with controlled displacements. At least one device including a light source emitting a light beam whose characteristics depend on the inclination of the conveyor belt, interacts with a network of photodiodes capable of emitting an electrical signal for controlling the jacks supporting the nondeformable structure in order to maintain the reference planes of the framework continuously exactly parallel to the plane of the conveyor belt whatever the inclination of the latter.

The three jacks each include a rod which moves in translation, preferably connected by means of a block of elastic material to a support base of the chassis.

Each support base fits at its upper end into an appropriate housing in the framework. In one preferred embodiment, the upper end of the support bases and the corresponding housings are of frustoconical shape.

By virtue of the existence of the blocks of elastic material, the shear forces which are exerted on the three supports of the framework are absorbed whatever the variations in inclination of the framework caused by the movements of the rods of the three jacks so as to match the inclination of the conveyor belt.

In a preferred embodiment of the invention, two rectilinear light sources are arranged exactly perpendicular to the reference planes and spaced apart from each other. Both light sources each emit a pencil of white light which is partially occulted by the frame of the conveyor belt. Two linear arrays of photodiodes interact with the two light sources. For this purpose, the arrays of photodiodes are placed at the focus of an optical focussing device, arranged so as to receive the two partially occulted pencils of light. Means are furthermore provided in order to determine at any instant the number of photodiodes illuminated in each array and in order to emit signals for controlling the jacks in order to maintain the reference plane exactly parallel to the plane of the conveyor belt. By virtue of these two light sources it is furthermore possible to determine at any instant the elevation of the conveyor belt with respect to the reference planes of the framework.

A light emitter, such as a laser, is in addition solidly fixed to the frame of the conveyor so as to emit a thin light beam exactly perpendicular to the conveyor belt. This emitter interacts with an optical system, preferably of the anamorphic type, solidly fixed to the framework, and capable of converting the thin light beam into a planar light pencil substantially parallel to the vertical plane in which the inclination of the frame is adjustable. A linear array of photodiodes is arranged perpendicular to the trace of this light pencil. Means are provided in order to determine the diode or diodes in the said array illuminated by the said light pencil and in order to emit a signal for controlling the jacks in order to maintain the reference plane parallel to the plane of the conveyor belt.

The invention will be better understood on studying the detailed description of one embodiment taken by way of example which is in no way limiting and which is illustrated by the attached drawings in which:

DETAILED DESCRIPTION OF THE PREFERRED EMBODIMENTS

The embodiment illustrated in a mounting framework for the drawings relates to the contactless testing of glass bottles directly on output from molding at high temperature. It will, of course, be understood that the invention may also be applied to the testing of other molded objects insofar as the same type of problem is encountered and in particular to molded objects made of plastic.

Figure 1:
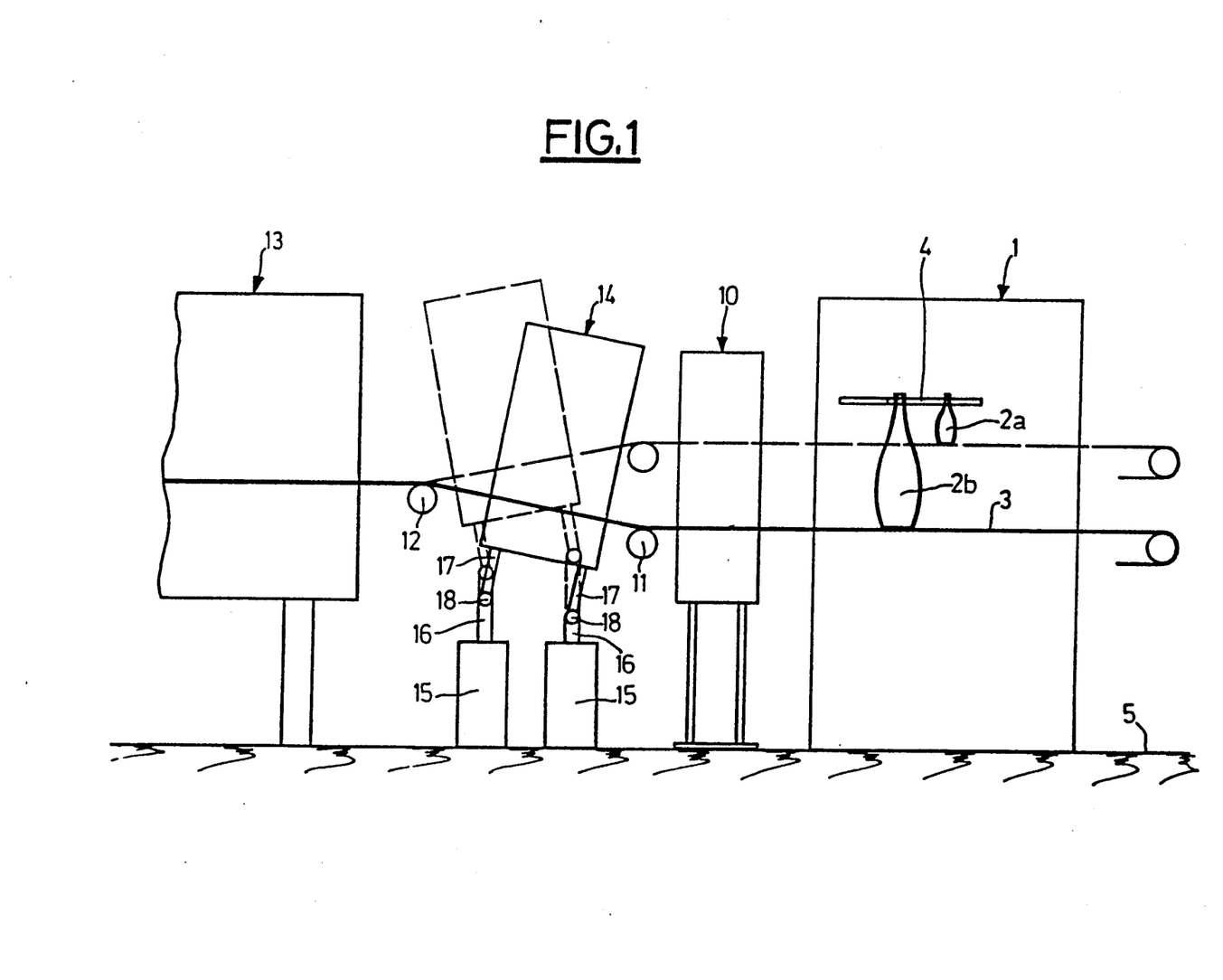
FIG. 1 is a highly schematic elevation view of the main elements of a glass bottle molding installation; according to the present invention

As illustrated in FIG. 1, the installation comprises a molding machine 1 including several independent sections for molding glass bottles. The bottles, whose size may vary, for example between a small bottle 2a and a large bottle 2b, are displaced at the output of the molding machine 1, on a conveyor belt 3 of which only the upper belt branch has been represented in order to simplify the figure. The bottles are extracted after molding by means of a gripper 4 or "take out" whose axis is at a constant level with respect to the ground 5 on which the machine 1 is installed.

Figure 2:
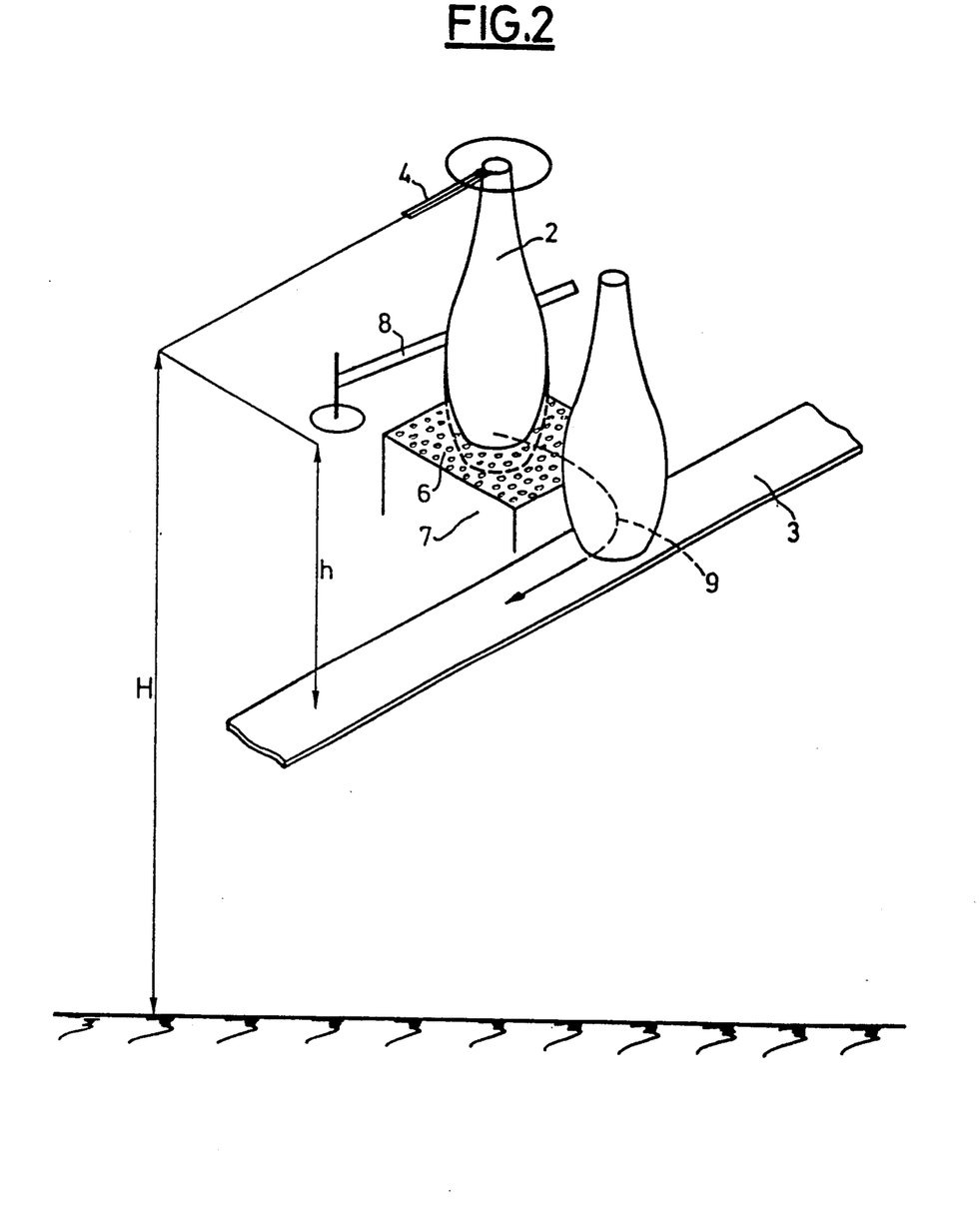
FIG. 2 is an enlarged schematic perspective view of the device for gripping the bottle on output from the mold, also showing its displacement on the conveyor belt.

With reference to FIG. 2, which illustrates the extraction of a molded bottle 2 on a larger scale, it is seen that this bottle is grasped by the gripper 4 which extracts it from the mold which is not represented in FIG. 2, by a pivotal movement in a horizontal plane. The bottle 2 held by its neck at its top, is placed above a perforated plate 6 which is situated at the upper part of a box 7 subjected to a current of cold air. The cold air leaves through the holes 6 and causes cooling or "hardening" of the bottle which has just come out of the mold of the manufacturing machine. When this cooling is finished, that is to say after a time of a few fractions of a second, the gripper 4 deposits the bottle 2 on the plate 6, the new position of the bottle 2 being illustrated in FIG. 2 by dotted lines. Then a rotating push rod 8 pivots and acts on the bottle 2 so as to displace it in the direction of the arrow 9 until it is on the conveyor belt 3, furthermore communicating to it in this movement a speed substantially equal to the speed of displacement of the conveyor 3. In FIG. 2, the constant height H of the axis of the gripper 4 with respect to the ground 5 and the variable height h of the upper surface of the conveyor 3 with respect to the axis of the gripper 4 as a function of the height of the bottles 2, have furthermore been represented.

Referring again to FIG. 1, it is seen that because of the fixed height position of the axis of the gripper 4, it is necessary to displace the conveyor 3 vertically in order to allow it to receive bottles of large dimensions 2b as well as bottles of small dimensions 2a. The conveyor belt 3 may therefore move opposite the molding machine 1 from a low position illustrated by a solid line to a high position illustrated by broken lines. The conveyor belt 3 may of course adopt other intermediate positions as a function of the size of the desired bottles.

The bottles 2 transported by the conveyor 3 pass through, on output from the manufacturing machine 1, a hot treatment hood 10 which allows for example the deposition of a fine layer of tin tetrachloride, for example in order to close the microcracks of the bottles which have just been manufactured. After this first treatment, the conveyor 3 passes over a roller 11 which can move vertically according to the position of the conveyor belt. At the end of its path, the conveyor belt 3 passes over a second stationary roller 12 in front of an oven 13 called a "lehr" into which a plurality of bottles are introduced in rows perpendicular to the path of the conveyor belt 3 by being pushed inside the lehr 13 by a pushing instrument not represented in FIG. 1.

Since the belt of the lehr 13 is at a constant level, the conveyor belt 3 must also stay at a constant level in front of the lehr 13. The conveyor belt 3 must as a result have an adjustable inclination between the rollers 11 and 12. Now, it is precisely at this location that it is preferable to perform the various hot tests on the bottles 2 immediately on output from the manufacturing.

The schematic illustration of the mounting framework 14 of the present invention is seen in Figure 1, mounted on the ground 5 by means of jacks 15, of which only two are schematically illustrated in FIG. 1. The jacks 15 include rods 16 which can move vertically and which are connected to the support bases 17 of the framework 14 via blocks 18 made of an elastic material, for example rubber or neoprene, which is capable of absorbing the shear forces The invention makes it possible to maintain the same inclination for the mounting framework 14 as for the conveyor belt 3 in the zone for hot testing of the bottles, the mounting framework 14 being able to occupy a first position illustrated by a solid line for the bottles 2b of large dimensions and a second position represented in broken lines for the bottles 2a of small dimensions. By virtue of the modification in inclination of the framework 14, the various testing devices which may be mounted on the framework 14 always stay in a constant position with respect to the conveyor belt 3, that is to say with respect to the bottles 2 to be tested.

Figure 3:
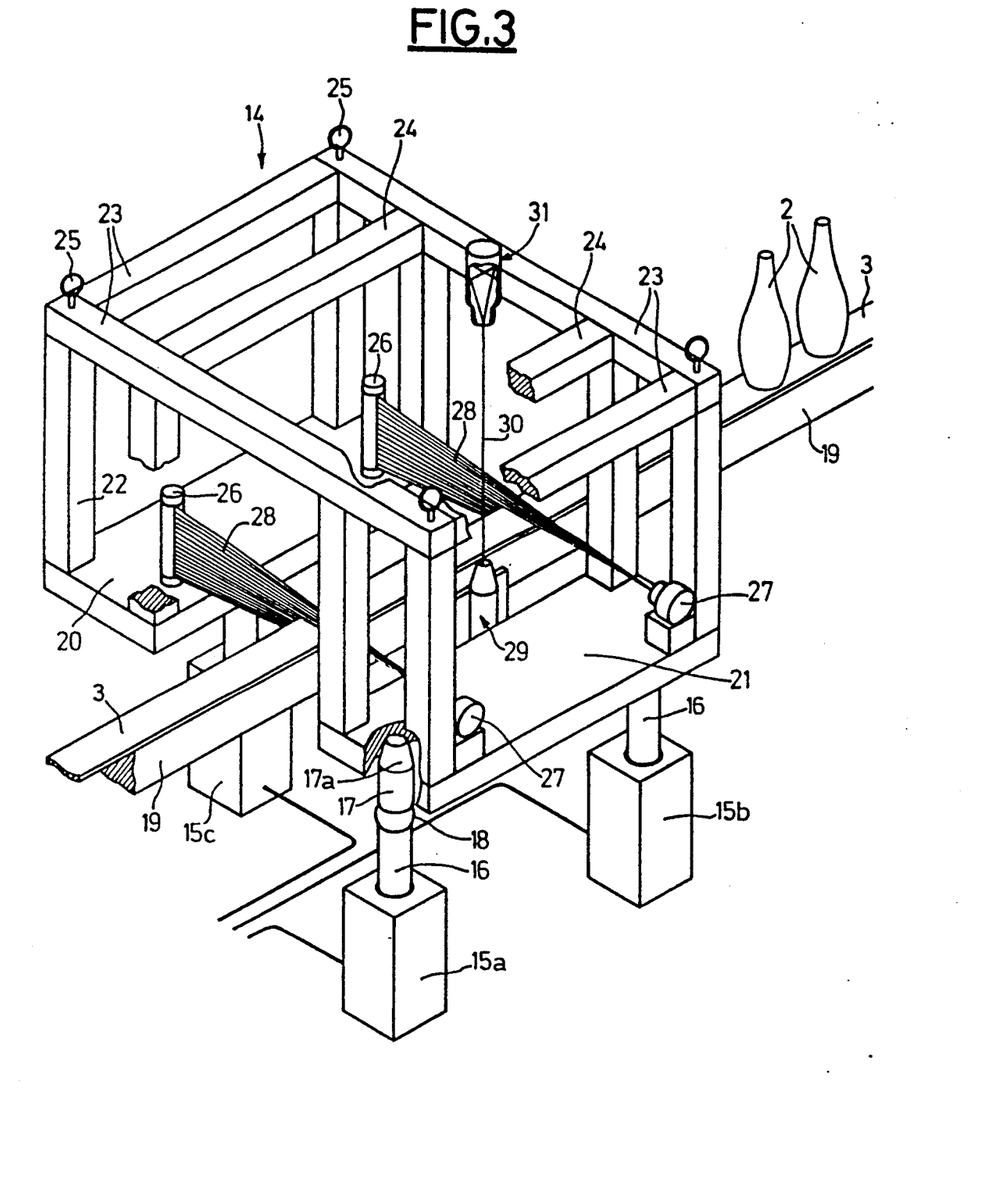
FIG. 3 is a partially exploded schematic perspective view of a mounting framework according to the invention, showing the assembly arranged above a conveyor belt.

FIG. 3 illustrates the general structure of the mounting framework 14. The mounting framework 14 is made in the form of a nondeformable structure which straddles the conveyor belt 3 and its stationary frame 19 in the manner of a bridge. The nondeformable structure of the framework 14 comprises, in the embodiment illustrated, two lower plates 20, 21 situated in the same plane, defining a lower reference plane for the mounting framework 14. The lower plane is situated slightly beneath the plane of the conveyor belt 3 which moves longitudinally between the two plates 20, 21. Eight rigid and nondeformable columns referenced 22 are mounted respectively at the four corners of the two plates 20, 21 and connected to a horizontal upper support frame consisting of four bars 23 which are also rigid and nondeformable. Two additional bars 24 situated above the edges of the two facing plates 20, 21 are also situated in the plane of the upper support frame and increase the rigidity of the whole of the structure. The bars 23, 24 define a second upper reference plane for the mounting framework 14, the upper reference plane being perfectly parallel to the lower reference plane.

The set of columns 22, 23, 24 like the plates 20, 21 is made of a heavy material which has a coefficient of thermal expansion close to zero so as to produce a rigid, mechanically nondeformable structure whatever the temperature of the objects such as the glass bottles 2 which pass through the framework 14 while being displaced on the conveyor belt 3.

It will be understood that it is easy to arrange the various desired optical or optoelectronic measurement and testing means on the two reference planes and on the various columns 22 or the bars 23, 24, in order to carry out the set of tests on the bottles 2 at high temperature when the latter pass through the mounting framework 14. These measurement devices are not represented in FIG. 3.

The mounting framework 14 is supported with respect to the ground by three jacks 15a, 15b and 15c, the two jacks 15a, 15b supporting the plate 21 while the third jack 15c supports, substantially in its median zone, the plate 20. The three jacks 15a, 15b and 15c are preferably electromechanical jacks which are self-locking in the absence of an electric current. The rods 16 of the three jacks are guided and may move vertically without play. At the end of the rods 16 there are blocks of elastic material 18 via which the rods 16 are connected to the bases 17, only one of which has been represented in FIG. 3, the other bases being identical. The end 17a of the support bases 17 are of frustoconical shape and fit into corresponding housings, also of frustoconical shape, made in the thickness of the plates 21 and 20. Under these conditions, the bases 17 are rigidly connected, by being fitted, to the plates 20 and 21, the compensation for the inclination and for the shear forces being made solely by the elastic joints 18.

The particular form 17a of the ends of the support bases 17, which thus allows the fitting, allows easy extraction of the whole of the mounting framework, which may be displaced by means of a hoist and slings, not represented in the figure, which interact with lifting hooks 25. For installation or cleaning operations, it is therefore easy to extract the assembly of the mounting framework 14, the three jacks 15a, 15b, 15c staying fixed to the ground and carrying the three bases 17 at the end of their respective rods 16. The mounting framework 14 may then be easily reinstalled in position by simply lowering it onto the three bases 17.

The automatic control of the inclination of the mounting framework 14 as a function of that of the conveyor belt 3 is produced in the example illustrated by means of three separate devices. The first two, which are identical, each consist of a rectilinear light source 26 mounted on the lower plate 20 perpendicular to the plane of the latter, that is to say perpendicular to the lower reference plane. The two light sources 26 are spaced apart from each other, being arranged in the vicinity of the two extreme edges of the plate 20 so as to direct a vertical pencil 28 of white light towards the conveyor belt 3 and its stationary frame 19. Opposite the two light sources 26, two optoelectronic devices 27 are placed, mounted on the plate 21 so as to receive the light pencil coming from the light sources 26 after partial occultation by the frame 19 and the conveyor 3 and after suitable focussing. In fact, taking into account the position of the lower reference plane, consisting of the upper surface of the two plates 20 and 21, the light sources 26 are made so that the light pencils 28 emitted are partially occulted, preferably substantially half-occulted, by the conveyor belt 3 and its stationary frame 19.

The third device consists for example of a laser emitter 29, solidly fixed to the support 19 of the conveyor 3, which emitter is fixed to the frame 19 so as to emit a thin light beam 30 exactly perpendicular to the plane of the conveyor belt 3. An optoelectronic device 31 is fixed to the upper support frame consisting of the horizontal bars 23, in a position such that it can receive the laser beam 30.

The three optoelectronic devices 27 and 31 are capable of emitting an electrical signal for controlling the various jacks 15a, 15b and 15c in order to maintain the lower and upper reference planes continuously strictly parallel to the plane of the conveyor belt 3, whatever its inclination.

Figure 4:
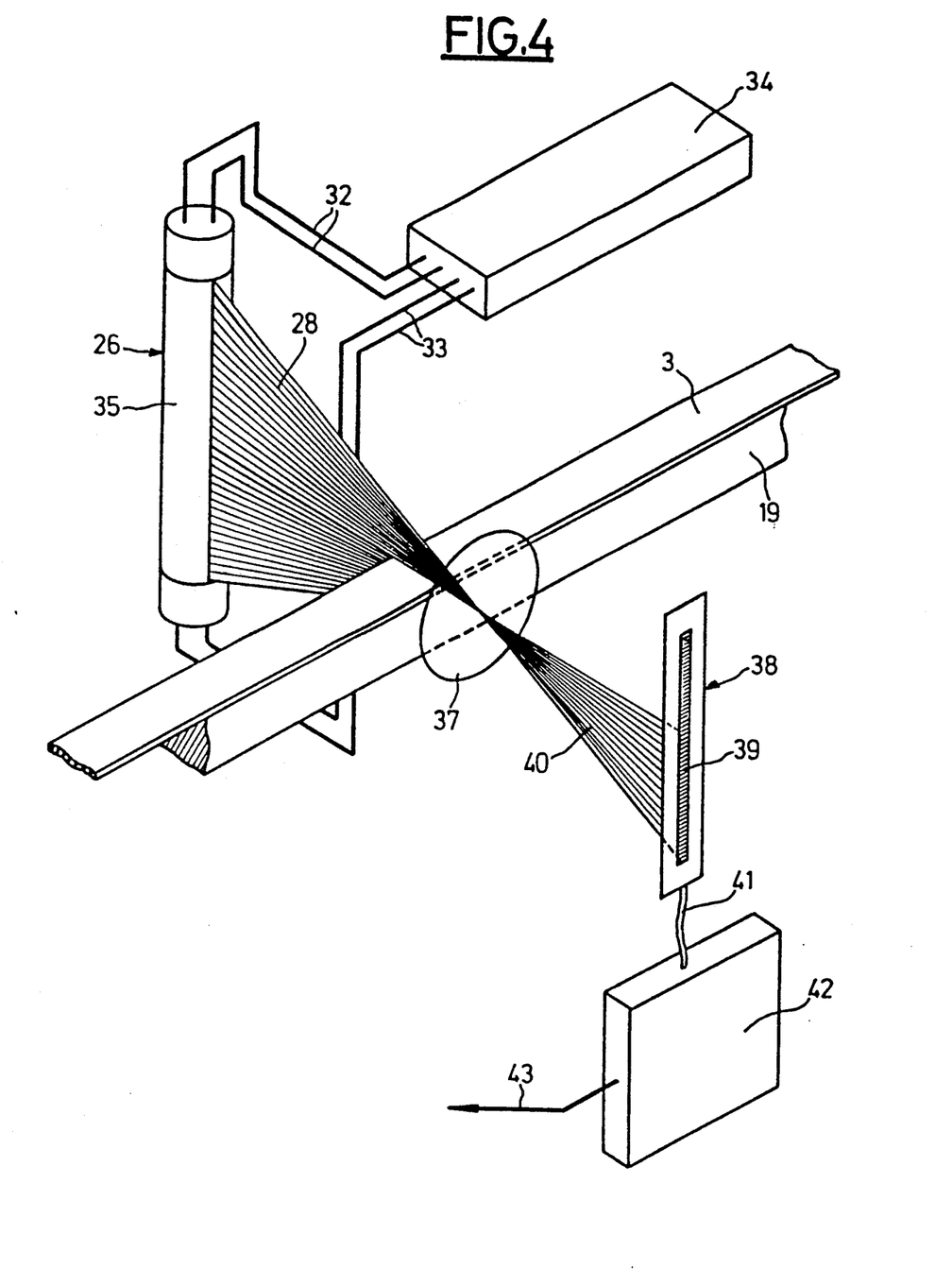
FIG. 4 is a partial schematic view of one of the light sources, interacting with a linear array of photodiodes, which receives the partially occulted light pencil.

Reference will now be made to FIG. 4, in order to explain the operation of one of the means for controlling the jacks, including one of the vertical light sources 26. In the embodiment illustrated in FIG. 4, the strip light 26 consists of a fluorescent tube, the longitudinal axis of which is perfectly perpendicular to the lower reference plane defined by the plate 20 visible in FIG. 3. The fluorescent tube 26 is powered with an electric current through the connections 32, 33 connected to a high-frequency convertor 34. The convertor 34 powers the fluorescent tube 26 with a current at high frequency, for example of the order of 25 kHz in order to utilize the afterglow of the light discharge in the tube 26 in order to obtain a continuous light emission, that is to say without scintillation. The fluorescent tube 26 advantageously includes a mask 35, defining a slot which allows the narrow vertical light pencil 28 to pass, directed perpendicular to the conveyor belt 3 and toward the latter so as to be partially occulted by the stationary frame 19 which constitutes an opaque obstacle for the light pencil 28.

On the other side of the conveyor belt 3 from the light source 26, a conventional focussing optical instrument 37 is arranged, which directs the partially occulted light pencil onto a linear array of photodiodes 38 placed at the focus of the optical instrument 37, and including a plurality of photodiodes 39, for example N photodiodes. The light beam 28 partially occulted by the frame 19 becomes a partial light pencil 40 when it reaches the array of photodiodes 38 thus illuminating a certain number of the photodiodes 39 while others are not illuminated. Taking into account the position of the frame 19, it appears that a proportion of the diodes 39 which are at the upper end of the array 38 do not receive light rays since this proportion corresponds to the occulted zone of the light pencil 28 while other diodes 39 situated at the lower, part of the array 38 receive the light rays of the light pencil 40.

The array of photodiodes 38 is connected by the electrical connection 41 to a microprocessor 42 capable of emitting through an output connection 43 a signal which is used to control the jacks 15a, 15b and 15c.

Figure 6A:
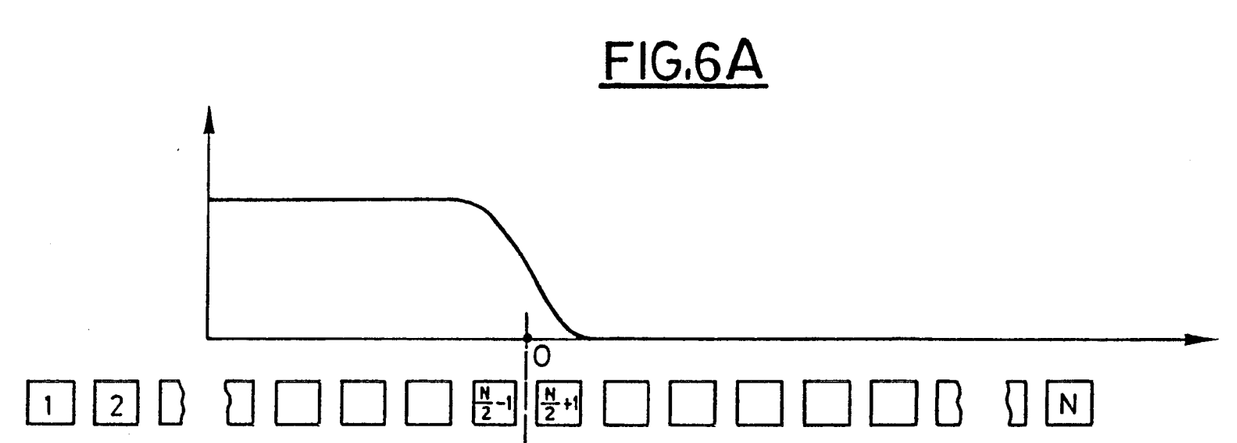
FIGS. 6A and 6B illustrate the determination of the transition between the illuminated diodes and the occulted diodes in FIG. 4.
Figure 6B:
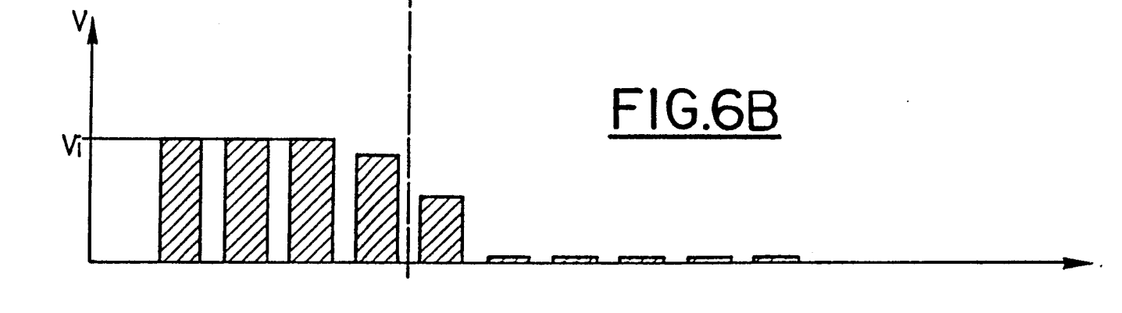

The detection of the exact position of the point of transition on the network of photodiodes 38 is illustrated in FIGS. 6A and 6B in the case of a network with an even number of photodiodes 39. The photodiodes 39 are labeled by a number from 1 to N, the axis O of the network of photodiodes being situated between diode $N/2-1$ and diode $N/2+1$.

The light amplitude as a function of the diode number is represented on the upper graph in FIG. 6A which shows that a proportion of the diodes 39, in the example illustrated, the diodes from number 1 to $N/2-1$ are completely illuminated by the light pencil 40 (FIG. 4).

A light intensity v results which is illustrated as a function of the diode numbers on the lower graph in FIG. 6B which is constant for all these diodes. The diode numbered $N/2+1$ which is substantially at the location of the transition only receives a light intensity which is substantially less than half the light intensity v of the preceding diodes.

It is therefore easy to locate the transition between two adjacent photodiodes, the separation between two photodiodes being generally of the order of 25 μm.

The automatic control is preferably designed so that the set-point value for the signals for controlling the jacks 15a, 15b, 15c locates the transition substantially at the center O of the network of photodiodes 38, in the case of both networks of photodiodes 38, so as to maintain the inclination of the mounting framework identical to that of the conveyor belt 3, that is to say to maintain the reference planes strictly parallel to the plane of the conveyor belt 3. In addition, the position of the transition points on the networks of photodiodes 38 makes it possible to measure at any instant the elevation of the transporter belt 3 with respect to the reference plane consisting of the plates 20, 21.

It will be noted that means are provided to stop the transfer of the measurement signals when an object situated on the conveyor occults the light beam.

Figure 5:
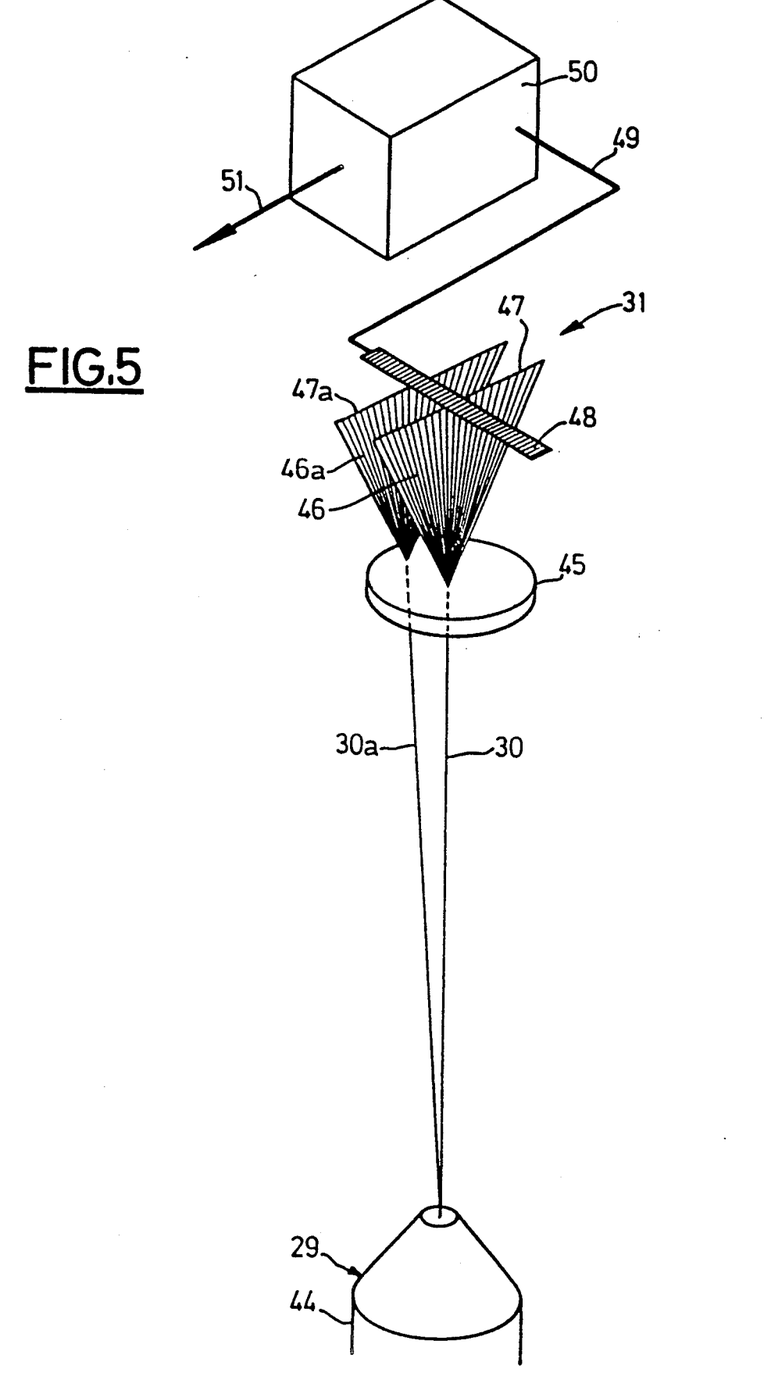
FIG. 5 is a schematic view of the laser emitter and of its associated linear array of photodiodes.

FIG. 5 illustrates in an enlarged manner the optoelectronic device 31 interacting with the laser beam 30. A protective cap 44 of the laser emitter 29 which emits the laser beam 30 is seen in FIG. 5. The laser emitter 29 is fixed on a support which is solidly fixed to the frame 19 of the conveyor belt 3 so as to be exactly perpendicular to the plane of the conveyor belt 3. An anamorphic optical system 45 receives the laser beam 30 and converts it into a substantially vertical planar light pencil 46 whose trace 47 is perpendicular to a linear network of photodiodes 48 placed in the reference plane of the mounting framework 14 perpendicular to the axis of the conveyor belt 3. The network of photodiodes 48 is connected through an electrical connection 49 to a microprocessor 50 which generates a signal through an output connection 51, being used to control the jacks 15a, 15b, 15c.

A variation in a relative inclination between the reference plane of the mounting framework 14 and the frame 19 of the conveyor belt 3 leads to an angular variation of the laser beam 30 which adopts for example the position 30a illustrated in FIG. 5. A planar luminous pencil 46a results, whose trace 47a is displaced with respect to the network of photodiodes 48.

The determination of the position of the light spot corresponding to the trace 47 on the network of photodiodes 48 makes it possible to act on the control of the jacks 15a, 15b, 15c. A set-point value is preferably chosen for the adjustment such that the position of the light spot corresponding to the trace 47 coincides with the axis of the network of photodiodes 48.

It will now be explained with reference to the diagrams in FIGS. 7A and 7B how it is possible to determine the exact position of the trace 47 on the network of photodiodes 48.

Figure 7A:
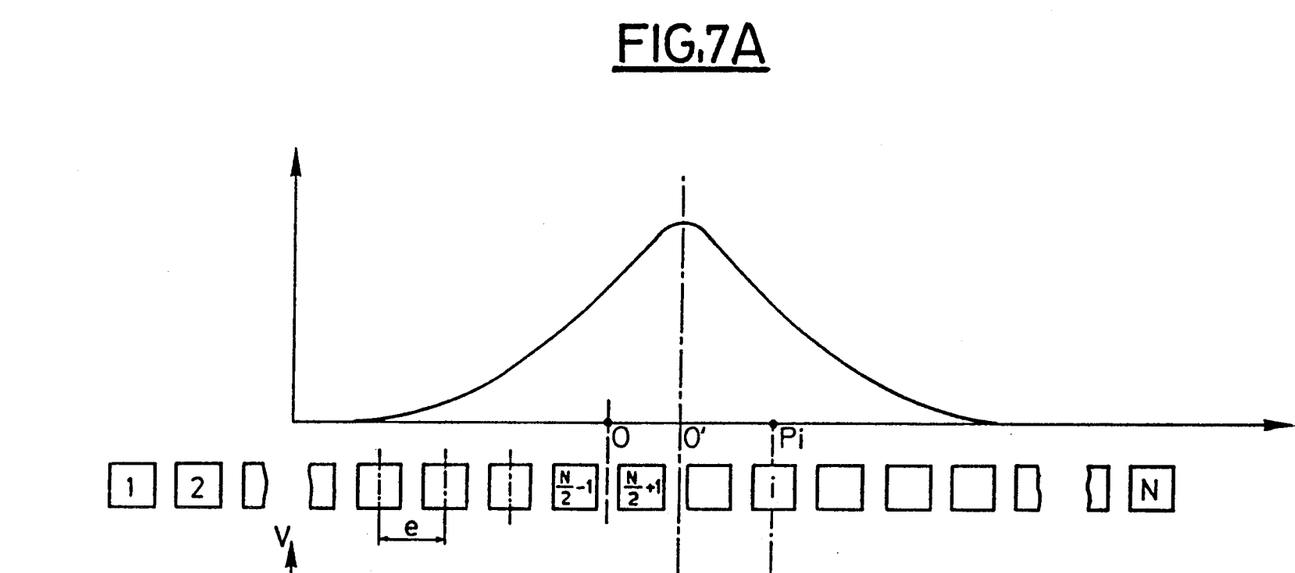
FIGS. 7A and 7B illustrate the determination of the position of the light spot on the array of photodiodes in FIG. 5.

The graph of FIG. 7A shows the value of the light amplitude of the light spot formed on the array of photodiodes 48 by the light pencil 46 as a function of the number of the diode in question, each diode being labeled by a number going from 1 to N. Since the thickness of the light pencil 46 is not infinitely low, neither is the light spot received by the network of photodiodes 48 infinitely small. It has the appearance of a bell curve whose axis of symmetry is the axis passing through the point O' in FIG. 7A. Several diodes are therefore simultaneously lit up by the said light spot. In the example illustrated, the network of photodiodes 48 includes an even number of photodiodes. The center of the network is constituted by the point 0 situated between diode $N/2-1$ and diode $N/2+1$.

Figure 7B:
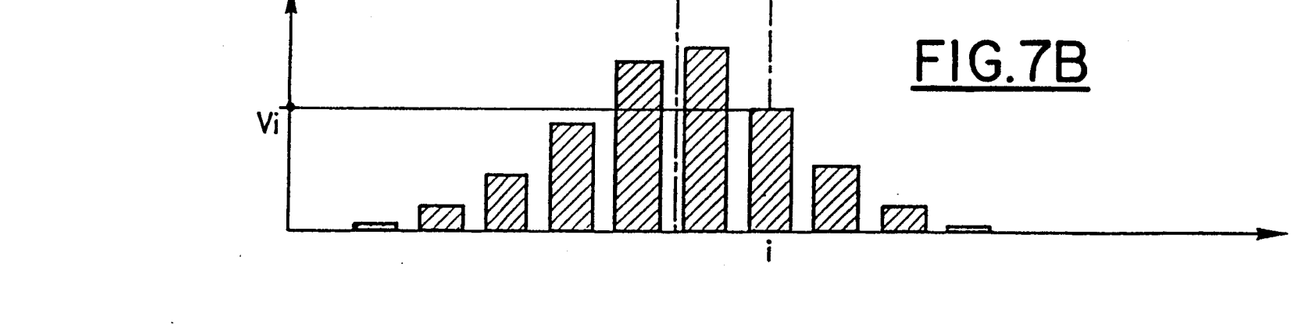

The graph in FIG. 7B shows the value of the light intensity v for the various diodes illuminated by the light spot as a function of the diode number. For each diode, its center is labeled by the point $P_i$ corresponding to the diode of order i, the latter receiving a light intensity $v_i$.

The microprocessor 50 is capable of determining distance between the center of the light spot O' and the center of the network 0 for the network with an even number of diodes.

Assuming that the light distribution curve is symmetrical, which it is in practice, the following equation may be written:

$$\sum_{i=1}^{N} \overline{O'P_i} \cdot v_i = 0 \tag{I}$$

The unknown to be found $x = \overline{OO'}$ is then obtained geometrically from equation (I) and has the value:

$$x = \overline{OO'} = \frac{\sum_{i=1}^{N} \overline{OP_i} \cdot v_i}{\sum_{i=1}^{N} v_i} \tag{II}$$

If the distance between the center of two neighboring photodiodes is defined to be e, the distance between the center of the photodiode i and the center O of the network may be calculated therefrom to be:

$$\overline{OP_i} = (n_i + N/2)e + e/2 \quad (III)$$

Substituting this value into equation (II) the value of x to be found is finally obtained:

$$x = \frac{\sum_{i=1}^{N} e\left(n_i - \frac{N}{2} + \frac{1}{2}\right)v_i}{\sum_{i=1}^{N} v_i} \quad (IV)$$

where x is the distance between the center 0 of the network of photodiodes for an even number of diodes and the center O' of the light spot;

e is the distance between the centers of two neighboring photodiodes;

$n_i$ is the number of a diode indexed i;

N is the total number of photodiodes in a network which, in the example, is an even number, generally 128 or 512;

and $v_i$ is the light intensity received by the photodiode i.

In order to maintain the inclination of the mounting framework 14 exactly equal at any instant to the inclination of the conveyor belt 3, a set-point value is then defined for the adjustment which is preferably such that the axis O' of the light spot substantially coincides with the axis O of the network of photodiodes 39.

Figure 8:
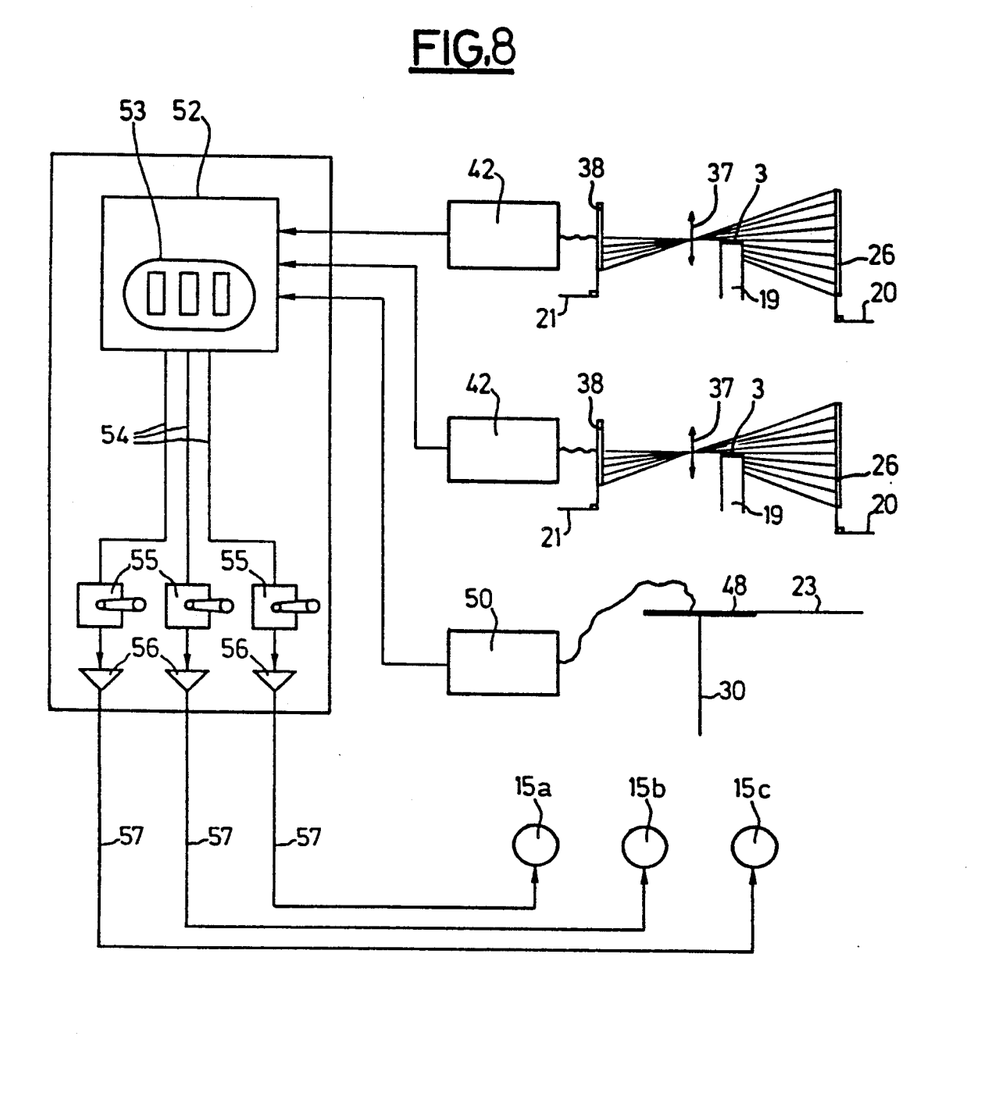
FIG. 8 is a block diagram of the control assembly of the support jacks of the framework.

FIG. 8 diagrammatically shows the principal elements of the device of the invention. The two light sources 26 are schematically indicated therein as being mounted, perpendicular to the lower reference plane defined by of the plate 20. The light pencils focused by the optical device 37 which are occulted by the frame 19 illuminate the lower portion of the network of photodiodes 38 which are arranged perpendicular to the lower reference plane constituted by the plate 21. The signals emitted, after having been processed by the microprocessors 42, each associated with one network of photodiodes 39, are conveyed to a computer 52. Under the same conditions, the laser beam 30 produces a light spot on the network of photodiodes 48 solidly fixed to the upper reference plane constituted for example by a horizontal bar 23. The signal emitted, after having been processed by the microprocessor 50 is also conveyed to the computer 52. The latter includes a display panel 53 allowing the operation of the device and the emission of the signals output by the microprocessors 42 and 50 to be monitored at any instant. The output signals of the computer 52 are conveyed through the connections 54 via manual control devices to power amplifiers 56 each connected through a respective connection 57 to one of the jacks 15a, 15b and 15c.

By virtue of the mounting framework of the present invention, it is possible to maintain the nondeformable structure of the framework in a stationary position with respect to the conveyor belt, whatever the inclination of the latter and in a simple and perfectly reliable manner even in a hostile environment such as that of an installation for manufacturing glass bottles. The conveyor belt 3 is in no way trapped by the device which may on the contrary be easily retracted and repositioned without it being necessary to shut down the whole of the installation.

Any desired measurement and testing devices may easily be mounted inside the nondeformable structure of the mounting framework of the invention so as to perform the desired tests for the glass bottles moving on the conveyor belt.

I claim:

1. A mounting framework for mounting contactless testing devices for testing molded objects, in particular glass objects, at high temperature, comprising a conveyor belt for supporting molded objects, said conveyor belt being driven with respect to a frame of the conveyor belt with an adjustable inclination in the same vertical plane; first and second means defining two parallel reference planes and connected to each other by rigid columns so as to define a nondeformable structure straddling the conveyor belt in the manner of a bridge, said structure being disconnected from said frame of the conveyor belt; three jacks which are controlably displaceable and supporting said structure; and at least one optical device including a light source emitting alight beam whose characteristics depend on the inclination of the conveyor belt, and generating an electrical signal in response thereto, said photodiodes being operatively connected to said jacks for controlling said jacks so as to maintain the reference planes of the structure continuously parallel to a plane of the conveyor belt at any of inclined positions thereof.

2. The framework according to claim 1, wherein the three jacks each include a movable rod, a block of elastic material connected thereto, and a support base connected to said block and received in the nondeformable structure.

3. The framework according to claim 2, wherein each support base includes an upper end which fits into a respective housing provided in said nondeformable structure.

4. The framework according to claim 3, wherein the upper end of each support base and corresponding housings of the nondeformable structure for receiving the upper ends are of frustoconical shape.

5. The framework according to claim 1, wherein said at lest one optical device includes two rectilinear light sources perpendicular to the reference planes and being spaced apart from each other, each light source emitting a pencil of white light partially occulted by the frame of the conveyor belt, interacting with two linear arrays of photodiodes of said network of photodiodes, and an optical focussing device, said photodiodes being placed at the focus of said optical focussing device so that said arrays are illuminated by both partially occulted light pencils, and means for determining at any instant the number of photodiodes illuminated in each array and generating signals for controlling the jacks in order to maintain the reference planes parallel to the conveyor belt.

6. The framework according to claim 5, wherein the light sources are fluorescent tubes powered at a frequency greater than an afterglow of the fluorescent tubes.

7. The framework according to claim 5 wherein a microprocessor is provided for each array of photodiodes which is associated with a respective microprocessor receiving the signals emitted by the arrays of photodiodes and storing set-point values of positions of the various light beams, said set-point values being selected so that a transition signal corresponds each time substantially to a median zone of each array of photodiodes.

8. The framework according to claim 5, and further comprising an anamorphic optical system; a light emitter rigidly fixed to the frame of the conveyor belt so as to emit a thin light beam (30) exactly perpendicular to the plane of the conveyor belt and interacting with said anamorphic optical system, said anamorphic optical system being rigidly fixed to the undeformable structure and capable of converting the thin light beam into a planar light pencil substantially parallel to a vertical plane in which the inclination of the frame of the conveyor belt is adjustable; a linear array of photodiodes arranged perpendicular to a trace of said planar light pencil; and means for determining at any instant at least one photodiode of said linear array illuminated by said light pencil and generating a signal for controlling the jacks in order to maintain the reference planes parallel to the plane of the conveyor belt.

9. The framework according to claim 8, and further comprising an additional microprocessor and wherein the linear array of photodiodes is associated with said additional microprocessor receiving signals emitted by the linear array of photodiodes and storing a set-point value of the position of the trace of the planar light pencil, said set-point value being selected so that the trace of the planar light pencil sub-stantially corresponds to an axis of the linear array of photodiodes.

10. The framework according to claim 8 wherein the light emitter is a laser emitter.

* * * * *